United States Patent [19]

Holý et al.

[11] Patent Number: 5,733,896

[45] Date of Patent: Mar. 31, 1998

[54] N-(3-FLUORO-2-PHOSPHONYLMETHOXYPROPYL) DERIVATIVES OF PURINE AND PYRIMIDINE HETEROCYCLIC BASES, THEIR PREPARATION AND USE

[75] Inventors: Antonin Holý, Horni Počernice; Jindřich Jindřich, Praha, both of Czechoslovakia; Erik De Clercq, Parklaan; Jan Balzarini, Egenhoven, both of Belgium

[73] Assignees: Institute of Organic Chemistry and Biochemistry of the Academy of Sciences of the Czech Republic, Czech Rep.; Rega Stichting v.z.w., Belgium

[21] Appl. No.: 210,255

[22] Filed: Mar. 18, 1994

Related U.S. Application Data

[63] Continuation of Ser. No. 29,368, Mar. 10, 1993, abandoned, which is a continuation of Ser. No. 685,866, Apr. 16, 1991, abandoned.

[30] Foreign Application Priority Data

Apr. 24, 1990 [CS] Czechoslovakia ............... 2047-90

[51] Int. Cl.[6] .................. A61K 31/675; C07F 9/6512; C07F 9/58; C07F 9/6521
[52] U.S. Cl. ................ 514/81; 544/243; 544/244; 546/23
[58] Field of Search ............... 544/243, 244; 514/81, 86; 546/23

[56] References Cited

U.S. PATENT DOCUMENTS

| | | | |
|---|---|---|---|
| 4,199,574 | 4/1980 | Schaeffer | 544/27 X |
| 4,495,190 | 1/1985 | Hagberg et al. | 514/262 |
| 4,808,419 | 2/1989 | Holy et al. | 544/244 |
| 4,988,680 | 1/1991 | Halazy et al. | 514/81 |
| 5,047,533 | 9/1991 | Reist et al. | 544/244 |

FOREIGN PATENT DOCUMENTS

| | | | |
|---|---|---|---|
| 253412 | 1/1988 | European Pat. Off. | 544/243 |
| 0338887 | 10/1989 | European Pat. Off. | 544/276 |
| 0096589 | 4/1990 | Japan | 544/243 |

OTHER PUBLICATIONS

Connolly, Anti Microbial Agents & Chems. 36, p. 245 (1992).
De Clerq, AIDS Res. S. Ham. Retrovirus 8, 119(1992).
Dr. Sandstrom Letter of Jun. 19, 1990.
Mansuri et al. Chemtech, 564 (Sep. 1992).
Saari, J Med Chem 35, 3792 (1992).
Merck Stndby Statement of Sep. 4, 1993.
Antiviral Agents Bulletin 6, p. 260 (Sep. 1990).
Antiviral Agents Bulletin 6, p. 162 (Jun. 1993).
Holy, et al., Nucleotide Analogues, 1989, American Chemical Society, Chapter 4, pp. 51–71.
Bronson, et al., Nucleotidex Analoques, 1989, American Chemical Society, Chapter 5, pp. 72–87.
Balzarini, et al., J. Biol. Chem, vol. 266(14), pp. 8686–8689 (1991).
Balzarini, et al., Biochem. Biphys Res. Commun., vol. 178, No. 1, pp. 329–335 (1991).
Coates et al, Ant. Microb. Agents & Chemo Therapy 36, 733(1992).
Kong et al, Anti Microb. Agents & Chemotherapy 35, 2003 (1991).
Koch et al. Antiviral Research 19, 81–109 (1992).
Translation of JP2–096589 (1990).
Kim, J Med Chem 33, 1207 (1990).
Balzarini, Proc. Natl. Acad Sci 88, 4961(1991).
Balzarini, et al., "5–Phosphoribosyl 1–Pyrophosphate Synthetase Converts the Acyclic . . . " The Journal of Biological Chemistry, vol. 266, No. 14, Issue May 15, pp. 8686–8689, 1991.
Balzarini, et al., "Activity of Acyclic Nucleoside Phosphonate Analogues Against . . . " Biochemical and Biophysical Research Communications, vol. 178, No.,1, pp. 329–335 Jul. 15, 1991.
Balzarini et al, "Differential Antiherpesvirus and Antiretrovirus Effects of the (S) and )R) Enantiomers of Acyclic Nucleoside Phosphonates: Potent and Selective In Vitro Antiretrovirus Activities of (R)–9–(2–Phosphonomethoxypropyl)–2,6–Diaminopurine", Anti Microb Agents Chemother, vol. 37(2), pp. 332–338 (1993).
Chu et al, "Chemistry and Antivral Activities of Acyclonucleosides", J. Hetero Chem. vol. 23, pp. 289–319 (1986).
De Clercq et al, "Broad–spectrum antiviral activity of adenosine analogues", Antiviral Research, vol. 4, pp. 119–133 (1984).
Dvorakova et al, "Synthesis and Biological Effects of 9–(3–Hydroxy–2–Phosphonomethoxypropyl) Derivatives of Deazapurine Bases", Collect Czech Chem Commun, vol. 58, pp. 1403–1418 (1993).
Dvorakova et al, "Synthesis and Antiviral Activity of Acyclic Nucleoside and Nucleotide Derivatives of 8–Azaadenine", Collect Czech Chem Commun, vol. 58, pp. 253–255 (1993).
Dvorakova et al, "Synthesis and Biological Effects of N–(2–Phosphonomethoxyethyl) Derivatives of Deazapurine Bases", Collect Czech Chem Commun, vol. 58, pp. 1419–1429 (1993).

(List continued on next page.)

Primary Examiner—Mark L. Berch
Attorney, Agent, or Firm—Max D. Hensley

[57] ABSTRACT

N-(3-Fluoro-2-phosphonylmethoxypropyl) derivatives of purine and pyrimidine heterocyclic bases, method of producing them and their use as active principles of drugs.

The invention relates to suppression of multiplication of viruses, particularly retroviruses, by application of the new compounds, N-(3-fluoro-2-phosphonylmethoxypropyl) derivatives of purine and pyrimidine heterocyclic bases. These compounds are obtained by the reaction of the N-(3-fluoro-2-hydroxypropyl) derivatives of purine and pyrimidine heterocyclic bases with diesters of p-toluenesulfonyloxymethylphosphonic acid in the presence of sodium hydride.

16 Claims, No Drawings

OTHER PUBLICATIONS

Vahlenkamp et al. "(R)-9-(2-Phosphonylmethoxypropyl)-2,6-Diaminopurine Is a Potent Inhibitor of Feline Immunodeficiency Virus Infection," Antimicro AG & Chemo 39(3):746-749 (1995).

Antiviral Agents Bulletin 6, Aug. 1993, p. 228.

Flexner et al, Antimicrob. Agents Chemo. 35 (1991, p. 2544.

Staal, AIDS Res & Hamon Ret. 9, 299(1993).

Saunders, Drug Design & Discovery 8, 1992, p. 255.

Fields, Virology, 2nd ed., vol. 2, pp. 1439, 1449-1450 (Raven Press, Ltd. 1990).

Weininger, "Organic Chemistry" (Academic Press, 1984) pp. 201-203.

N-(3-FLUORO-2-PHOSPHONYLMETHOXYPROPYL) DERIVATIVES OF PURINE AND PYRIMIDINE HETEROCYCLIC BASES, THEIR PREPARATION AND USE

This is a continuation of application Ser. No. 08/029,368 filed on Mar. 10, 1993 abandoned which is a continuation, of application Ser. No. 07/685,866, filed Apr. 16, 1991 abandoned.

This invention relates to N-(3-fluoro-2-phosphonylmethoxypropyl) derivative of purine and pyrimidine heterocyclic bases methods of their preparation and their use as active principles of drugs.

Particularly dangerous among viral diseases are those caused by retroviruses, such as HIV which induces AIDS. Curing of these infections is very difficult and although several compounds of widely varying structure (sulfated polysaccharides, aurine-tricarboxylic acid, Evans Blue, glycyrrhizine, heparine, tetrahydroimidazo[4,5,1-jk][1,4] benzodiazepine-2(1H)-thiones, etc.) show significant effects in tissue cultures, only modified analogs of nucleosides and nucleotides (2',3'-dideoxycytidine, 2',3'-dideoxy-2',3'-didehydrothymidine) have been efficient in the treatment of experimental animals. For the therapy of AIDS, only 3'-azide-2',3'-dideoxythymidine (AZT, zidovudin) and 2',3'-dideoxyinosine (ddI) have so far been approved.

Another important group of compounds that are, inter alia, active against retroviruses, is represented by acyclic nucleotide analogs, e.g. 9-(2-phosphonylmethoxyethyl) purines (Czechoslovak Author's Certificate No 263951) of which the adenine derivative PMEA was studied most intensively (Czechoslovak Author's Certificate No 263952). Tests with experimental animals have proven its effect on Moloney sarcoma virus, murine leukemia virus, simian immunodefficiency virus (SIV), and in tissue cultures also on HIV (E. DeClercq, Antiviral Res. 12, 1 (1989)).

Remarkable is the narrow structural margin of these compounds, whose activity is sensitive to any structural modifications made in the side-chain of the 2-phosphonylmethoxyethyl group. Introduction of alkyl groups, elongation or shortening of the chain or removal of the oxygen atom leads invariably to loss of the antiviral activity (A. Holý, E. DeClercq, I. Votruba: Nucleotide Analogues as Antiviral Agents, ACS Symposium Series No 401, p. 51 (1989)). The only substitution which does not result in the loss of antiviral activity is introduction of a hydroxymethyl group into the position 2 of the side-chain; however, such derivatives are active exclusively against DNA viruses (herpesviruses, adenoviruses, poxviruses etc.) (Czechoslovak Author's Certificate No 233665 and 264222) whereas the antiretroviral effect is lost. The corresponding aminomethyl, alkoxymethyl and azidomethyl derivatives show no antiviral activity, the same being true for compounds in which the hydroxymethyl group is replaced by a methyl group (A. Holý, E. DeClercq, I. Votruba: Nucleotide Analogues as Antiviral Agents. ACS Symposium Series No 401, p. 51 (1989)).

This invention relates to N-(3-fluoro-2-phosphonylmethoxypropyl) derivatives of purine and pyrimidine heterocyclic bases of the general Formula I

wherein B denotes a purin-9-yl or pyrimidin-1-yl moiety and the absolute configuration at the C-2 carbon atom is S, R or RS, and their salts with alkali metals, ammonia or amines.

The invention further relates to the method of producing compounds of the general formula I, which consists in reaction of N-(3-fluoro-2-hydroxypropyl) derivatives of pyrimidine and purine heterocyclic bases of the general formula II

where B' is a purin-9-yl or pyrimidin-1-yl moiety or its derivatives protected with O-alkyl, N-acyl or N-dialkylaminomethylene groups, and the absolute configuration at the C-2 carbon atom is S, R or RS, with dialkyl p-toluenesulfonyloxymethylphosphonates of the general formula III

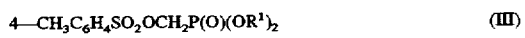

wherein $R^1$ is an alkyl ($C_1$-$C_3$), preferably 2-propyl group, in the presence of 1–5 molar equivalents (related to compounds of the general formula II) of sodium hydride in a dipolar aprotic solvent, preferably dimethylformamide, at temperatures –30° C. to 100° C., whereupon the solvent is evaporated and the protecting group on the heterocyclic base is removed by methanolysis or acid hydrolysis and, after isolation or detonization at room temperature, the compounds of the general formula IV

wherein B signifies the same as in the formula I and $R^1$ is the same as in formula III, are reacted with bromotrimethylsilane in an aprotic solvent, preferably in acetonitrile, and after removal of the solvent the reaction mixture is treated with water or buffer solutions and the compounds of the general formula I are isolated, preferably by ion-exchange chromatography.

This invention relates further to a method of producing the compound of general formula I, where B is hypoxanthin-9-yl, consisting in reaction of compound of the formula I, where B is adenin-9-yl, with 3-methylbutyl nitrite in 50–80% aqueous acetic acid or with an aqueous solution of sodium nitrite in the presence of an equimolecular amount of acetic acid at room temperature.

Further, the invention relates to the method of producing the compound of formula I, wherein B is xanthin-9-yl, consisting in reaction of compound of formula I, where B is guanin-9-yl, with 3-methylbutyl nitrite in 50–80% aqueous acetic acid or with an aqueous solution of sodium nitrite in the presence of an equimolecular amount of acetic acid at room temperature.

Further, the invention relates to the method of producing the compound of Formula I, wherein B is 2,6-diaminoadenin-9-yl, consisting in reaction of compound of Formula I, where B is 2-amino-6-azido-purin-9-yl, with gaseous hydrogen in the presence of a catalyst, preferably metallic palladium, prereduced on an inorganic carrier, in water or in dilute aqueous solutions of organic or mineral acids.

The invention also relates to a method of utilization of compounds of the general formula I for suppressing multiplication of viruses, particularly retroviruses, and application of these compounds to treatment of diseases caused by these viruses.

The pyrimidine bases in the general Formula I can be common natural bases such as uracil, thymine, cytosine, of the general formula V

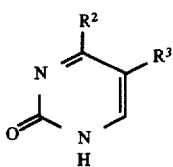

wherein R² is a hydrogen atom, a hydroxylamino, hydrazino, alkoxy, amine or substituted amino group and R³ is a hydrogen or halogen atom or an alkyl ($C_1$–$C_3$) group, or moieties of the general Formula VI

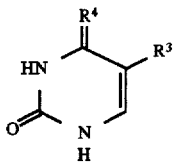

wherein R³ has the same signification as in the formula V, and R⁴ is an atom of oxygen or sulfur, but also their synthetic analogs such as aza (5-aza, 6-aza) or deaza (3-deaza) derivatives.

The purine bases in compounds of the general formula I may be natural bases such as e.g. adenine, hypoxanthine, guanine, xanthine, or generally moieties of the general formula VII

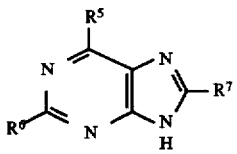

where R⁵ and R⁶ are a hydrogen or halogen atom, an amino, hydrazino, hydroxylamino, azide, substituted amino, hydroxy, alkoxy, mercapto, alkylmercapto group, or an alkyl group with a short carbon chain ($C_1$–$C_4$), and combination of these groups, and R⁷ is an atom of hydrogen or halogen, a hydroxy, alkoxy, mercapto, alkylthio, amine or substituted amine group; and their synthetic analogs, e.g. aza (2-aza, 8-aza) or deaza (1-deaza, 3-deaza or 7-deaza) derivatives.

Compounds of the general formula I can be prepared advantageously by the method according to this invention which is based on the introduction of a phosphonomethyl group to the free hydroxy group of N-(3-fluoro-2-hydroxypropyl) derivatives of heterocyclic bases of the general formula II. These compounds are well accessible e.g. by alkylation of heterocyclic bases with fluoromethyloxirane (Czechoslovak Patent Application PV 2048-90). To exclude side-reactions during the introduction of the organophosphorus synthon, those compounds of the formula II that contain a basic amino group (e.g. cytosine, adenine, guanine etc.) should be protected by introduction of a suitable protecting group, e.g. by aroylation (benzoylation), by transformation into the amidine functionality or otherwise (A. Holý, I. Rosenberg, H. Dvořáková: Collect. Czech. Chem. Commun. 54, 2470 (1989)), using e.g. the specific N-benzoylation method described by G. S. Ti, B. L. Gaffney, and R. A. Jones (J. Am. Chem. Soc. 104, 1316 (1982)).

The prepared protected derivatives of the general formula II are then condensed with the reagent of the general formula III in the presence of sodium hydride, preferably in dimethylformamide. Best results are obtained if the reaction is performed with 3-3.5 molar equivalents of the hydride (related to compound II). The alkylation reagent of the general formula III is obtained according to the previously described method (A. Holý, I. Rosenberg: Collect. Czech. Chem. Commun. 47, 3447 (1982); A. F. Kluge: Org. Syn. 64, 80 (1985)); the ester group may be an alkyl or an aralkyl group. Since however, under the given reaction conditions compounds of the formula III may (similarly as neutral esters of phosphoric and phosphonic acids) behave as alkylation reagents, it is advisable to use esters with a low alkylation potency such as e.g. the 2,2-dimethylpropyl or 2-propyl ester. The latter is easily accessible, e.g. by the procedure described in the next paragraph.

Triethylamine (8.4 ml) is added to a stirred mixture of di(2-propyl) phosphite (96 g) and paraformaldehyde (23 g), and the mixture is heated to 100° C. (reflux condenser, calcium chloride protecting group) until the parsformaldehyde dissolves completely. After heating for one more hour, the reaction mixture is cooled and mixed with acetonitrile (500 ml) and p-toluenesulfonyl chloride (121.5 g). Triethylamine (90 ml) and 4-dimethylaminopyridine are then added under stirring. After stirring for 24 h, the mixture is cooled with ice, 0.4M triethylammonium hydrogen carbonate (400 ml) is gradually added and the mixture is again stirred for 24 h. Acetonitrile is evaporated in vacuo (bath temperature below 40° C.) and the mixture is extracted with ether (3×200 ml). The ethereal extract is dried over sodium sulfate, filtered, and the solvent is evaporated in vacuo. The residue is dissolved in benzene (200 ml) and filtered through a column of silica gel (500 ml, prepared in benzene). The column is washed with benzene until impurities of higher $R_F$ are removed (monitoring by TLC on silica gel plates in chloroform) and then the product is eluted with ethyl acetate. After evaporation of the solvent in vacuo, the remaining oil is stirred with light petroleum (300 ml) to crystallization, the crystals are collected, washed with light petroleum and dried in vacuo. Yield 140 g of di(2-propyl) p-toluenesulfonyloxymethylphosphonate, m.p. 37.5° C. For $C_{14}H_{23}PO_6S$ (350.4) calculated: 47.98% C, 6.61% H, 8.86% P, 9.15% S; found: 48.15% C, 6.80% H, 9.02% 9.24% S.

The reaction of compounds of the formula III with anions of compounds of the formula II proceeds well at low temperatures (−10° C. to 0° C.); it also may be performed at elevated temperatures. The reaction mixture is worked up preferably by removal of the protecting group (if used) from the heterocyclic base and isolation of the diester of the general formula IV by chromatography either on silica gel or an ion-exchanger. Under the deionization conditions, the di(2-propyl)esters are stable even in dilute ammonia. After drying, compounds of the formula IV are subjected to reaction with bromotrimethylsilane or iodotrimethylsilane in dimethylformamide, chlorinated hydrocarbons or preferably in acetonitrile. The reaction proceeds usually smoothly at room temperature. After evaporation and codistillation of the residue with water, the crude compounds of the general formula I are purified, preferably by ion-exchange chromatography and are stored preferably in the form of well water-soluble and stable alkali metal salts.

Compounds of the general formula I contain in the position 2 of the side-chain an asymmetric carbon atom. The described method of preparation is completely identical for both enantiomers (R and S) as well as for the racemic derivative and depends on the character of the starting compound of the general formula II.

The effect of compounds of the formula I is documented in Table 1. The explicit effect against retroviruses is unexpected because all the hitherto known modifications of the hydroxymethyl group in the HPMP derivatives of the general formula VIII

(VIII)

where B signifies the same as in formula I, and all substitutions in the PME derivatives of the general formula IX

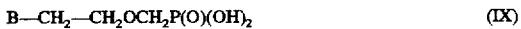

(IX)

where B denotes the same as in formula I, with any substituent other than a hydroxymethyl group, invariably resulted in compounds devoid of any antiviral activity. The replacement of the hydroxymethyl group in compounds of the general formula VIII with an atom of fluorine preserves thus unexpectedly the antiviral activity which at the same time is changed qualitatively to the selective antiretroviral activity, not corresponding to the effects of compounds of the general formula VIII or IX.

Compared with compounds of the general formula IX, compounds I have a better selectivity index (ratio of the mean minimum antiviral concentration to the mean cytotoxic concentration) which represents an important criterion in the development of potential antiviral drugs.

The method of preparing compounds of the general formula I according to this invention is illustrated by the following examples which do not represent any limitation; the antiviral activity of the prepared compounds is given in Table 1 and 2 which are a part of this invention.

EXAMPLES OF EXECUTION

Example 1

Chlorotrimethylsilane (24 ml) is added to a suspension of 9-(RS)-(3-fluoro-2-hydroxypropyl)adenine (6 g) in pyridine (160 ml) and the mixture is stirred at room temperature for 1 hour. Benzoyl chloride (18.5 ml) is added and the stirring at room temperature is continued for 2 hours. After cooling with ice, ice-cold water (30 ml) followed by concentrated aqueous ammonia (66 ml) is added and the mixture is stirred for 30 minutes under ice-cooling. The solid is collected, washed successively with water, acetone and ether and dried over phosphorus pentoxide at 15 Pa. Yield 7.5 g (84%) of 9-(RS)-(3-fluoro-2-hydroxypropyl)-$N^6$-benzoyladenine, m.p. 197° C., $R_F$=0.35 (TLC on Silufol UV 254 in chloroform-methanol 9:1). For $C_{15}H_{14}FN_5O_3$ (331.3) calculated: 54.38% C, 4.26% H, 5.73% F, 21.14% N; found: 54.62% C, 4.46% H, 6.04% F, 23.67% N. $^{13}$C NMR spectrum: 45.91 d, $CH_2N$, $^3J_{CF}$=8.0; 67.51 d, CH(OH), $^2J_{CF}$=19.2; 85.08 d, $CH_2F$, $^1J_{CF}$=169.1.

The obtained product is codistilled with dimethylformamide (2×25 ml) at 40° C./15 Pa, and dissolved in dimethylformamide (80 ml). The solution is cooled to 0° C., 60% dispersion of sodium hydride in paraffin oil (2.8 g) is added and the mixture is stirred for 30 minutes. A solution of di(2-propyl) p-toluenesulfonyloxymethylphosphonate (9.1 g) in dimethylformamide (20 ml) is added and the stirring is continued for 16 h at 80° C. under exclusion of moisture. After evaporation of the solvent at 40° C./15 Pa, the residue is codistilled under the same conditions with toluene (2×25 ml) and then 0.1M methanolic sodium methoxide (200 ml) is added. The mixture is allowed to stand at room temperature for 20 h, neutralized by addition of a cation-exchanging resin in the $H^+$-form (e.g. Dowex 50), made alkaline by addition of triethylamine and filtered. The solid on filter is washed with methanol (200 ml) and the combined filtrates are taken down in vacuo. The residue is applied onto a column of the same ion-exchanger (200 ml) which is then washed with 20% aqueous methanol. When the UV absorption (at 254 nm) of the eluate dropped to the original value, the product is eluted from the column with dilute (1:10 final concentration 2–2.5% wt/wt) aqueous ammonia solution (1 liter). The eluate is taken down in vacuo and the residue is codistilled with ethanol (2×50 ml), dried over phosphorus pentoxide at 15 Pa for 24 hours and mixed with acetonitrile (150 ml) and bromotrimethylsilane (15 ml). After standing for 24 hours at room temperature, the solvent is evaporated in vacuo, the residue is mixed with water (100 ml), set aside for 30 minutes and neutralized with concentrated aqueous ammonia. After evaporation in vacuo, the residue is dissolved in water (50 ml), applied on a column of a cation-exchanger (e.g. Dowex 50) in the $H^+$-form (200 ml) and the above-described deionization process is repeated. The ammonia eluate is evaporated and the residue, dissolved in water (50 ml) is applied onto a column of a medium basic anion-exchanger (e.g. Dowex 1×2) (200 ml). The column is washed with water (400 ml) and then successively with 0.5M acetic acid (1 liter) and 1M acetic acid, the elution course being monitored by measurement of the UV absorption of the eluate at 254 nm. The product is obtained from the 1M acetic acid eluate from which the acetic acid is removed by evaporation in vacuo and by codistillation of the residue with water. The product is dissolved in boiling water (100 ml), the solution is filtered while hot and concentrated in vacuo to about 20 ml. Ethanol (100 ml) and ether (100 ml) are added after standing for 24 h in a refrigerator, the product is collected, washed with ether and dried in vacuo. Yield 2.5 g of 9-(RS)-(3-fluoro-2-phosphonylmethoxypropyl)-adenine, m.p. 265° C. For $C_9H_{13}FN_5O_4P$ (305.3) calculated: 35.40% C, 4.29% H, 6.22% F, 22.95% N, 10.17% P; found: 35.69% C, 4.57% H, 7.25% F, 22.84% N, 9.71% P. $^{13}$C NMR spectrum: 43.12 d, $CH_2N$, $^3J_{CF}$=6.8; 77.47 dd, CH, $^2J_{CF}$=19.0; $^3J_{PC}$=11.0; 82.32 d, $CH_2F$, $^1J_{CF}$=167.3; 68.37 d, $CH_2P$, $^1J_{PC}$=149.8. Electrophoretical mobility (related to uridine 3'-phosphate) at pH 7.5: 0.88.

Example 2

Chlorotrimethylsilane (27 ml) is added to a suspension of 1-(RS)-(3-fluoro-2-hydroxypropyl)cytosine (5.9 g) in pyridine (180 ml) and the reaction mixture is further processed as described in Example 1. Yield 10 g of 1-(RS)-(3-fluoro-2-hydroxypropyl)-$N^4$-benzoylcytosine, m.p. 205° C. $R_F$=0.42 (TLC, Silufol UV 254, chloroform-methanol 9:1). For $C_{14}H_{14}FN_3O_2$ (291.3) calculated: 57.72% C, 4.84% H, 6.52% F, 14.43% N; found: 58.29% C, 4.63% H, 6.32% F, 14.19% N. $^{13}$C NMR spectrum: 45.91 d, $CH_2N$, $^3J_{CF}$=8.0; 67.51 d, CH(OH), $^2J_{CF}$=119.2; 85.08 d, $CH_2F$, $^1J_{CF}$=169.1.

This product is codistilled with dimethylformamide (2×25 ml) at 40° C./15 Pa, dissolved in dimethylformamide (100 ml), cooled to 0° C. and mixed with 60% dispersion (3.8 g) of sodium hydride in paraffin oil. After stirring for 30 minutes, a solution of di(2-propyl) p-toluene-sulfonyloxymethylphosphonate (11.6 g) in dimethylformamide (20 ml) is added and the mixture is stirred under exclusion of moisture for 16 hours at 80° C. Further work-up procedure, the reaction of the deionized intermediate with bromotrimethylsilane and the subsequent processing and deionization are performed as described in Example 1. The ammonia eluate is evaporated, the residue is dissolved in water (50 ml) and applied onto a column of a medium basic anion exchanger (e.g. Dowex 1×2; 200 ml). The column is washed with water (400 ml) and then the product is eluted with 0.5M acetic acid; its elution is monitored by UV absorption measurement (at 254 nm) of the eluate. The UV absorbing fractions are evaporated in vacuo and the residue is freed from acetic acid by codistillation with water and purified by preparative liquid chromatography on a column of C18-silica gel (300 ml) in water. The product is dissolved in boiling water (100 ml), the hot solution is filtered and concentrated in vacuo to about 20 ml. Ethanol (100 ml) and ether (100 ml) are added, the mixture is set aside in a refrigerator for 24 hours, filtered and the product washed with ether and dried in vacuo. Yield 2.0 g of 1-(RS)-(3-fluoro-2-phosphonylmethoxypropyl)-cytosine, m.p. 219° C. For $C_8H_{13}FN_3O_5P$ (281.3) calculated: 34.16% C, 4.66% H, 6.76% F, 14.94% N, 11.04% P; found: 34.63% C, 5.00% H, 6.70% F, 15.47% N, 11.15% P. $^{13}C$ NMR spectrum: 49.42 d, $CH_2N$, $^3J_{CF}$=7.1; 78.04 dd, CH, $^2J_{CF}$=18.5, $^3J_{PC}$=11.4; 82.78 d, $CH_2F$, $^1J_{CF}$=167.2; 67.70 d, $CH_2P$, $^1J_{PC}$=153.9. Electrophoretical mobility (relative to uridine 3'-phosphate) at pH 7.5:0.95.

Example 3

Chlorotrimethylsilane (17 ml) is added to a suspension of 9-(RS)-(3-fluoro-2-hydroxypropyl)guanine (4.7 g) in pyridine (120 ml) and, after stirring for 1 hour, benzoyl chloride (13 ml) is added. After 2 hours the mixture is decomposed at 0° C. with water (20 ml) and concentrated aqueous ammonia (45 ml) and worked up as described in Example 1. Yield 7.2 g of 9-(RS)-(3-fluoro-2-hydroxypropyl)-$N^2$-benzoylguanine, m.p. 178° C.; $R_F$=0.20 (TLC, Silufol UV 254, chloroform-methanol 9:1). For $C_{15}H_{14}FN_5O_3$ (331.3) calculated: 54.38% C, 4.26% H, 5.73% F, 21.14% N; found: 54.82% C, 5.07% H, 5.71% F, 21.29% N. $^{13}C$ NMR spectrum: 45.73 s, $CH_2N$, $^3J_{CF}$=7.1; 67.54 d, CH(OH), $^2J_{CF}$=19.5; 85.04 d, $CH_2F$, $^1J_{CF}$=168.5.

This product is codistilled with dimethylformamide (2×25 ml) at 40° C./15 Pa, dissolved in dimethylformamide (80 ml), cooled to −20° C. and mixed with 60% dispersion of sodium hydride in paraffin oil (2.4 g) and with a solution of di(2-propyl) p-toluenesulfonyloxymethylphosphonate (7.7 g) in dimethylformamide (20 ml). The mixture is stirred at 70° C. for 16 hours under exclusion of moisture. Further work-up of the mixture, reaction of the deionized intermediate with bromotrimethylsilane and the subsequent work-up and deionization are executed as described in Example 1. The ammonia eluate is evaporated and the residue is dissolved in water (50 ml) and applied onto a column of medium basic anion-exchanger (120 ml; e.g. Dowex 1×2). The column is washed with water (400 ml) and then the product is eluted with 0.5M acetic acid, the course of the elution being followed by measurement of the UV absorption of the eluate at 254 nm. The UV-absorbing eluate is taken down in vacuo and the acetic acid is removed by codistillation of the residue with water. The product is crystallized from water; yield 2.3 g of 9-(RS)-3-fluoro-2-phosphonylmethoxypropyl)guanine, not melting up to 300° C. For $C_9H_{13}FN_5O_5P$ (321.1) calculated: 33.64% C, 4.08% H, 5.91% F, 21.80% N, 9.66% P; found: 34.00% C, 3.75% H, 5.60% F, 21.87% N, 10.20% P. $^{13}C$ NMR spectrum: 42.22 d, $CH_2N$, $^3J_{CF}$=8.3; 77.52 dd, CH, $^2J_{CF}$=19.0, $^3J_{PC}$=11.3; 82–05 d, $CH_2F$, $^1J_{CF}$=166.8; 67.96 d, $CH_2P$, $^1J_{PC}$=150.1. Electrophoretical mobility (related to uridine 3'-phosphate) at pH 7.5:0.92.

Example 4

Chlorotrimethylsilane (8.5 ml) is added to a suspension of 9-(RS)-3-fluoro-2-hydroxypropyl)-2-amino-6-azidopurine (4.7 g) in pyridine (60 ml), the mixture is stirred for 1 h and then benzoyl chloride (6.5 ml) is added. After 2 hours the mixture is decomposed at 0° C. with water (10 ml) and concentrated aqueous ammonia (24 ml). The mixture is worked up as described in Example 1 to give 3.6 g of 9-(RS)-(3-fluoro-2-hydroxypropyl)-2-benzoylamino-6-azidopurine, m.p. 198° C., $R_F$=0.30 (TLC on Silufol UV 254, chloroform-methanol 9:1). For $C_{15}H_{13}FN_8O_2$ (356.3) calculated: 50.56% C, 3.68% H, 5.33% F, 31.45% N; found: 50.42% C, 4.08% H, 5.32% F, 31.25% N.

This product is codistilled with dimethylformamide (2×25 ml) at 40° C./15 Pa, dissolved in dimethylformamide (40 ml), cooled to −20° C. and mixed with 60% dispersion of sodium hydride in paraffin oil (1.1 g) and di (2-propyl) p-toluenesulfonyloxymethylphosphonate (3.8 g) in dimethylformamide (10 ml). The mixture is stirred at room temperature for 16 h under exclusion of moisture. Further work-up of the mixture, reaction of the deionized intermediate with bromotrimethylsilane (80 ml of acetonitrile and 8 ml of bromotrimethylsilane), the subsequent work-up and deionization are performed as described in Example 1. After washing out the salts with water from the cation-exchanger column, the product is eluted with a considerable retention with water. The product-containing fractions are taken down in vacuo and the residue is crystallized from water to give 2.4 g of 9-(RS)-(3-fluoro-2-phosphonylmethoxypropyl)-2-amino-6-azidopurine, not melting up to 260° C. For $C_9H_{12}FN_8O_4P$ (346.3) calculated: 31.21% C, 3.49% H, 5.49% F, 32.36% N, 8.96% P; found: 31.56% C, 3.70% H, 5.62% F, 32.56% N, 9.21% P. Electrophoretical mobility (related to uridine 3'-phosphate) at pH 7.5:0.92.

Example 5

Chlorotrimethylsilane (7 ml) is added to a suspension of 9-(RS)-3-fluoro-2-phosphonylmethoxypropyl)-3-deazaadenine (9 mmol) in pyridine (50 ml). After 1 hour benzoyl chloride (5.5 ml) is added. After further 2 hours the mixture is decomposed at 0° C. by gradual addition of water (7 ml) and concentrated aqueous ammonia (18 ml) and after 30 minutes the solvents are evaporated in vacuo at 0° C. The residue is codistilled in vacuo and chromatographed on a column of silica gel (200 ml) in chloroform. The product is eluted with chloroform-methanol (95:5). Evaporation of the solvents in vacuo afforded 1.60 g or 9-(RS)-(3-fluoro-2-phosphonylmethoxypropyl)-$N^6$-benzoyl-3-deazaadenine as an amorphous foam, $R_F$=0.12 (TLC on Silufol UV 254, chloroform-methanol 9:1).

This product is mixed with a solution of di(2-propyl) p-toluenesulfonyloxymethylphosphonate (2 g) in dimethylformamide (10 ml) and, after cooling to −15° C., 60% dispersion of sodium hydride in paraffin oil (600 mg) is added. The reaction mixture is stirred for 16 hours at room temperature under exclusion of moisture. Further work-up of the mixture, reaction of the deionized intermediate with bromotrimethylsilane (50 ml of acetonitrile and 5 ml of bromotrimethylsilane), the subsequent work-up and deionization are performed as described in Example 1. The column of the cation-exchanger is eluted with water. After washing out the salts, the product is eluted with dilute aqueous ammonia. The product-containing fractions are evaporated in vacuo and the residue is purified by preparative chromatography on C18-silica gel (elution with water). Yield 0.50 g of 9-(RS)-(3-fluoro-2-phosphonylmethoxypropyl)-3-deazaadenine, not melting up to 260° C. For $C_{10}H_{14}FN_4O_4P$ (304.3) calculated: 39.47% C, 4.64% H, 6.24% F, 18.42% N, 10.20% P; found: 39.80% C, 4.67% H, 6.38% F, 18.67% N, 10.50% P. Electrophoretical mobility (related to uridine 3'-phosphate) at pH 7.5:0.78.

Example 6

3-Methylbutyl nitrite (2 ml) is added to a suspension of 9-(RS)-(3-fluoro-2-phosphonylmethoxypropyl)adenine (200 ml) in 80% aqueous acetic acid (20 ml) and the mixture is allowed to stand at room temperature for 24 hours. After evaporation in vacuo, the residue is codistilled with water (4×20 ml) and applied on a column of a cation-exchanger in H⁺-form (150 ml, e.g. Dowex 50). The column is washed with water and the elution is followed by measurement of UV absorption of the eluate at 254 nm. The UV-absorbing fractions are combined and evaporated in vacuo and the residue is codistilled with ethanol (2×25 ml), mixed with ether and collected on filter. Yield 100 mg of 9-(RS)-(3-fluoro-2-phosphonylmethoxypropyl)hypoxanthine, not melting up to 260° C. For $C_9H_{12}FN_4O_5P$ (306.3) calculated: 35.29% C, 3.95% H, 6.20% F, 18.30% N, 10.13% P; found: 35.15% C, 4.12% H, 6.43% F, 18.70% N, 9.87% P. Electrophoretical mobility (related to uridine 3'-phosphate) at pH 7.5:0.83.

Example 7

A suspension of 9-(RS)-(3-fluoro-2-phosphonylmethoxypropyl)guanine in a mixture of 80% aqueous acetic acid (20 ml) and 3-methylbutyl nitrite (2 ml) is allowed to stand at room temperature for 24 hours and processed further as described in Example 5. Yield 100 mg of 9-(RS)-(3-fluoro-2-phosphonylmethoxypropyl)xanthine, not melting up to 260° C. For $C_9H_{12}FN_4O_6P$ (322.3) calculated: 33.54% C, 3.75% H, 5.90% F, 17.39% N, 9.63% P; found: 33.65% C, 3.90% H, 5.77% F, 17.56% N, 9.40% P. Electrophoretical mobility (related to uridine 3'-phosphate) at pH 7.5:0.78.

Example 8

To a suspension of 9-(RS)-(3-fluoro-2-phosphonylmethoxypropyl)-2-amino-6-azidopurine (200 mg) in 80% aqueous acetic acid (50 mg) is added 10% palladium on active carbon (200 mg) and the mixture is stirred in an atmosphere of hydrogen at atmospheric pressure for 24 hours. The reaction mixture is filtered, the catalyst washed with water and the filtrate codistilled with water (3×20 ml). The crude product is purified by chromatography on a column of C18 silica gel in water and, after evaporation, the product is dissolved in hot water, mixed with a fivefold volume of ethanol and ether is added to incipient turbidity. After standing in a refrigerator, the product is collected on filter, washed with ether and dried in vacuo. Yield 100 mg of 9-(RS)-(3-fluoro-2-phosphonylmethoxypropyl)-2,6-diaminopurine, not melting up to 260° C. For $C_9H_{14}FN_6O_4P$ (320.3) calculated: 33.75% C, 4.41% H, 5.93% F, 26.24% N, 9.69% P; found: 33.65% C, 3.95% H, 5.79% F, 26.56% N, 9.42% P. Electrophoretical mobility (related to uridine 3'-phosphate) at pH 7.5:0.70.

TABLE 1

Effect of compounds of the general formula I on multiplication of HIV-1 in tissue cultures of MT-4 cells

| | | μg · ml⁻¹ | | |
|---|---|---|---|---|
| Compound | B | ED₅₀ᵃ | CD₅₀ᵇ | SIᶜ |
| 1 | Adenin-9-yl | 11.2 | >1000 | >90 |
| 2 | Guanin-9-yl | 4.7 | 233 | 50 |
| IX | Adenin-9-yl | 2.0 | 14.2 | 7.2 |

ᵃDose, suppressing by 50% the cytopatogenic effect of HIV-1 in MT-4 cells;
ᵇdose, decreasing the viability of MT-4 cells to one half;
ᶜratio CD₅₀/ED₅₀.

TABLE 2

Effect of compounds of the general formula I on the evolution of an MSV-induced tumor in newborn NMRI mice

| Compound | B | Dose (mg/kg/day) | Median day of tumor formation | Median survival time (days) |
|---|---|---|---|---|
| 1 | Adenin-9-yl | 20 | >13 | — |
| | | 5 | 7.5 | 14.4 |
| | | 1 | 5.8 | 10.9 |
| 2 | Guanin-9-yl | 20 | >13 | 10 |
| | | 5 | 8.5 | 12.5 |
| | | 1 | 5.2 | 11.7 |
| IX | Adenin-9-yl | 20 | >13 | — |
| | | 5 | 10.1 | 17.2 |
| | | 1 | 6.1 | 14.7 |
| Control | | 0 | 5.3 | 11.6 |

What we claim is:

1. A compound of formula I

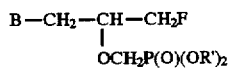    Formula I wherein R' is H or alkyl and B is a purin-9-yl base of formula VIIa

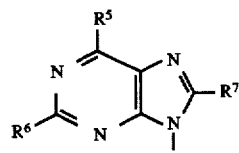    Formula VIIa wherein $R^5$ and $R^6$ are independently hydrogen, halogen, amino, hydrazino, hydroxylamine, azido, aroylamino, hydroxy, alkoxy, mercapto, alkylmercapto or $C_{1-4}$ alkyl, and $R^7$ is hydrogen, halogen, hydroxy, alkoxy, mercapto, alkylthio, amino or aroylamino, the 1-deaza, 3-deaza, 7-deaza, 2-aza or 8-aza analogues thereof, as the racemate or the (R) or (S) optical isomers thereof, or the pharmaceutically acceptable salts thereof with alkali metals, ammonia or amines.

2. A method of using a compound of formula II,

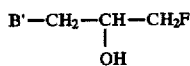    Formula II wherein B' is a purin-9-yl base or a protected form thereof, comprising the steps of;

(a) reacting said compound with a dialkyl p-toluenesulfonyloxymethyl phosphonate of the formula

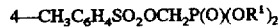    Formula III wherein $R^1$ is alkyl (1–3 C), in the presence of demethylformamide sodium hydride, (b) removing by methanalysis or acid hydrolysis the protection group on protected heterocyclic base B', (c) and isolating compounds of formula IV

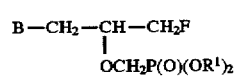    Formula IV wherein B is a purin-9-yl base.

(d) reacting the compound of formula IV with bromotrimethylsilane or iodotrimethylsilane in an aprotic solvent, and after removal of the solvent treating the reaction mixture with water or buffer solutions and isolating the compounds of formula I

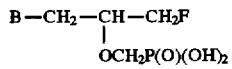  Formula I

3. A compound of formula

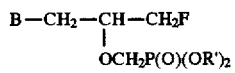  Formula I wherein, $R^1$ is H or alkyl, and B is a purin-9-yl base of formula VIIa

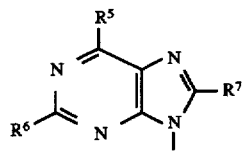  Formula VIIa wherein $R^5$ and $R^6$ are independently hydrogen, halogen, amino, hydrazino, hydroxylamine, azido, hydroxy, alkoxy, mercapto, alkylmercapto or $C_{1-4}$ alkyl, and $R^7$ is hydrogen, halogen, hydroxy, alkoxy, mercapto, amino or alkylthio, the 1-deaza, 3-deaza, 7-deaza, 2-aza or 8-aza analogues thereof, the (R) or (S) optical isomers thereof, or the pharmaceutically acceptable salts thereof with alkali metals, ammonia or amines, provided however, that $R^6$ or $R^7$ are omitted in the case of the 2-aza or 8-aza analogues, respectively, and $R^5$, $R^6$ or $R^7$ also may be protected amino wherein the protecting group protects an amino group of the Formula VII base during condensation of base of formula VII

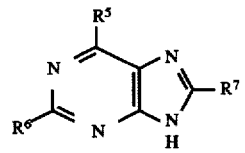  Formula VII with di(2-propyl) p-toluene-sulfonyloxymethylphosphonate and sodium hydride in dimethylformamide.

4. A method of suppressing multiplication of retroviruses in a host, comprising administering to the host a therapeutically effective amount of a compound of formula I

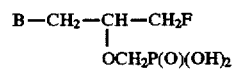  Formula I wherein B is a purin-9-yl base of formula VIIa

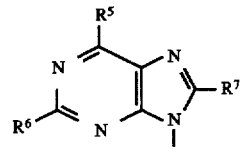  Formula VIIa wherein $R^5$ and $R^6$ are independently hydrogen, halogen, amino, hydrazino, hydroxylamine, azido, aroylamino, hydroxy, alkoxy, mercapto, alkylmercapto or $C_{1-4}$ alkyl, and $R^7$ is hydrogen, halogen, hydroxy, alkoxy, mercapto, amino or aroylamino, the 1-deaza, 3-deaza, 7-deaza, 2-aza or 8-aza analogues thereof, the (R) or (S) optical isomers thereof, or the pharmaceutically acceptable salts thereof with alkali metals, ammonia or amines, provided, however, that $R^5$ and $R^6$ are not both hydroxyl, and if $R^6$ is hydrogen then $R^5$ is not hydroxyl.

5. The compound of claim 1 which is the (R) optical isomer.

6. The compound of claim 1 wherein B is adenine or guanine.

7. The compound of claim 1 wherein B is a 3-deaza, 7-deaza, or 8-aza purin-9-yl base.

8. The compound of claim 1 wherein $R^5$ and $R^6$ independently are hydrogen, halogen, amino, hydrazino, hydroxylamine, azido, aroylamino, hydroxyl, alkoxy, mercapto or alkylmercapto, $R^2$ is hydrogen or halogen, and the aza or deaza analogues are the 3-deaza, 7-deaza or 8-aza analogues.

9. The method of claim 2 wherein $R^1$ is 2-propyl.

10. The compound of claim 8, wherein $R^5$ and $R^6$ independently are hydrogen, halogen, amino, hydrazino, hydroxylamine, aroylamino, hydroxyl, mercapto or alkoxy, $R^7$ is hydrogen and the aza or deaza analogue is 3-deaza.

11. The compound of claim 10 wherein $R^5$ and $R^6$ independently are hydrogen, halogen, amino or hydroxyl and the aza or deaza analogue is 3-deaza.

12. The compound of claim 11 wherein B is 3-deazaadenine.

13. The compound of claim 1 wherein B is not a 1-deaza, 3-deaza, 7-deaza, 2-aza or 8-aza analogue.

14. The compound of claim 13 wherein $R^7$ is hydrogen.

15. A method according to claim 4, wherein the host is a mammal.

16. A method according to claim 4, wherein the host is mammalian cell.

* * * * *